(12) United States Patent
Kraemer et al.

(10) Patent No.: US 9,026,238 B2
(45) Date of Patent: May 5, 2015

(54) CAD SYSTEM FOR ASSESSING BLANK SIZE

(75) Inventors: Michael A. Kraemer, Landsberg am Lech (DE); Guenter Hertlein, Seefeld (DE)

(73) Assignee: 3M Innovative Properties Company, St. Paul, MN (US)

( * ) Notice: Subject to any disclaimer, the term of this patent is extended or adjusted under 35 U.S.C. 154(b) by 1604 days.

(21) Appl. No.: 12/373,206

(22) PCT Filed: Jun. 29, 2007

(86) PCT No.: PCT/US2007/072487
§ 371 (c)(1),
(2), (4) Date: Dec. 1, 2010

(87) PCT Pub. No.: WO2008/008647
PCT Pub. Date: Jan. 17, 2008

(65) Prior Publication Data
US 2011/0071798 A1    Mar. 24, 2011

(30) Foreign Application Priority Data
Jul. 13, 2006 (EP) .................................... 06014625

(51) Int. Cl.
*G06F 19/00* (2011.01)
*A61C 11/00* (2006.01) *A61C 9/00*
(2006.01) *A61B 5/117*
(2006.01) *A61C 13/00*
(2006.01)

(52) U.S. Cl.
CPC ......... *A61C 13/0004* (2013.01); *A61C 13/0022* (2013.01)

(58) Field of Classification Search
CPC ...................................................... A61C 1/00
USPC ........... 700/97, 98, 118; 433/201.1, 213, 215, 433/229
See application file for complete search history.

(56) References Cited

U.S. PATENT DOCUMENTS 5,607,305 A * 3/1997 Andersson et al. ........... 433/223
2002/0102520 A1   8/2002 Iiyama et al.
(Continued)

FOREIGN PATENT DOCUMENTS

| EP | 1 614 396 | 1/2006 |
|---|---|---|
| WO | WO 99/13797 | 3/1999 |
| WO | WO 2005/007007 A2 | 1/2005 |

OTHER PUBLICATIONS

Shreiner, Dave et al. Open GL(R) Reference Manual: The Official Reference Document to OpenGL, Version 1.4., 4$^{th}$ Edition. Boston: Addison-Wesley Professional, 2004.
(Continued)

*Primary Examiner* — Mohammad Ali
*Assistant Examiner* — Ziaul Karim
(74) *Attorney, Agent, or Firm* — X. Christina Huang (57) ABSTRACT

In general the invention is directed to computer implemented systems and methods for assessing the size of a dental restoration blank. In one embodiment, the invention provides a computer-readable medium comprising dental CAD application code which implements the following procedures: generating in a computer memory a three dimensional digital rendering of a dental restoration; generating in the computer a digital rendering of a blank volume, the blank volume corresponding in dimensions to the usable volume of a blank that is available for milling, and the blank volume having a boundary corresponding to its edges; calculating areas of the dental restoration which are beyond the boundary; and providing the calculated areas to a calling function, user, user interface, or module.

18 Claims, 5 Drawing Sheets

(56) References Cited

U.S. PATENT DOCUMENTS

2005/0008887 A1* 1/2005 Haymann et al. .......... 428/542.8
2006/0008774 A1   1/2006 Orth et al.
2006/0122719 A1* 6/2006 Kopelman et al. .............. 700/98
2006/0177792 A1* 8/2006 Touchstone .................... 433/26
2007/0154868 A1* 7/2007 Scharlack et al. ............ 433/215

OTHER PUBLICATIONS

MeshLab website, May 31, 2006 at http://meshlab.sourceforge.net.
Neider, OpenGL Programming Guide, The Official Guide to Learning OpenGL, Release 1, Feb. 1993, <http://www.opengl.org/documentation/red_book/>, 5 pages.
OpenGL, The Industry's Foundation for High Performance Graphics, Website Copyright 1997, Khronos Group, [retrieved from the internet on Mar. 10, 2009], <www.opengl.org>, 6 pages.
OpenInventor a manual by Mercury Computer Systems Inc., Jun. 2008, htt://www.tgs.com/support/oiv_doc/UsersGuide/UsersGuide.pdf, 16 pages.
Rost, Open GL® Shading Language, $2^{nd}$ Edition. Boston: Addison-Wesley Professional, Jan. 2006, 15 pages.
Shreiner, OpenGI Programming Guide: The Official Guide to Learning OpenGL, Version 2 ($5^{th}$ Edition), Jul. 2005, 15 pages.

* cited by examiner

CAD SYSTEM FOR ASSESSING BLANK SIZE

CROSS REFERENCE TO RELATED APPLICATIONS

This application is a national stage filing under 35 U.S.C. 371 of PCT/US2007/072487, filed Jun. 29, 2007, which claims priority to EP Application No. 06014625.5, filed Jul. 13, 2006, the disclosure of which is incorporated by reference in its/their entirety herein.

The invention generally relates to systems, methods, and interfaces for assessing whether a dental restoration will exceed the usable size of a milling medium.

BACKGROUND

Existing software systems running on a computer allow a user to design a dental restoration, such as a cap, which fits over a tooth stump, or a pontic, which replaces a missing tooth and attaches to adjacent teeth stumps. A model of the dental restoration is then milled from a blank, which is, for example, a cube or cylinder of a ceramic material. The blanks, and the milling machine, have size limits, and the user may go through a lengthy design process to find her dental restoration exceeds the size limits.

One approach to determining of size of the blank in advance of design is to use a plastic apparatus with an area corresponding to an available blank's size removed. The plastic apparatus may be transparent. A user may then physically place the apparatus over a model of the tooth stump and try to determine the appropriateness of the size of the blank. This is technique is imprecise and does not account for eventual build-up of the dental restoration.

Another approach is to check the size of the dental restoration after the design is completed, just before milling. The size of the design, it may be found, is incompatible with the size of the blank, and the user must then redesign the dental restoration.

SUMMARY

In general, the invention is directed to methods, computer-implemented systems or methods, and computer-readable mediums having computer-readable instructions allowing a user to determine whether a dental restoration will likely exceed the size limits of a blank or milling machine before the user has invested much time designing the dental restoration. The invention may also allow a user to understand the size limits of a dental restoration before designing the restoration, thus allowing the user to design the restoration in a way that does not exceed the size limits, or accommodates the limitations in a workable solution.

In one embodiment, the invention is directed to a computer-readable medium having computer-readable instructions which implement the following procedures: generating in a user interface a three dimensional graphical rendering of a dental restoration; generating in the user interface a three dimensional graphical rendering of a three dimensional blank volume, the blank volume corresponding in dimensions to the useable portion of a blank that can be used for milling, wherein the graphical rendering of the three dimensional blank volume is overlaid upon the three dimensional graphical rendering of the dental restoration such that the three dimensional rendering of the dental restoration appears substantially inside of the three dimensional graphical rendering of the blank volume; and, based on the three dimensional blank volume overlaid upon the three dimensional graphical rendering of the dental restoration, determining what portion of the area of the dental restoration extends beyond the boundary of the three dimensional blank volume.

In another embodiment, the invention is directed to a computer-readable medium comprising dental CAD application code which implements the following procedures generating in a computer memory a three dimensional digital rendering of a dental restoration; generating in the computer a digital rendering of a blank volume, the blank volume corresponding in dimensions to the usable volume of a blank that is available for milling, and the blank volume having a boundary corresponding to its edges; before the design of a dental restoration is complete, calculating areas of the dental restoration which are beyond the boundary; and providing the calculated areas to a calling function, user, or module.

In another embodiment, the invention is directed to a method comprising: generating in a user interface a three dimensional graphical rendering of a dental restoration; generating in the user interface a three dimensional graphical rendering of a three dimensional blank volume, the blank volume corresponding in dimensions to the useable portion of a blank that can be used for milling, wherein the graphical rendering of the three dimensional blank volume is overlaid upon the three dimensional graphical rendering of the dental restoration such that the three dimensional rendering of the dental restoration appears substantially inside of the three dimensional graphical rendering of the blank volume; and, based on the three dimensional blank volume overlaid upon the three dimensional graphical rendering of the dental restoration, determining what portion of the area of the dental restoration extends beyond the boundary of the three dimensional blank volume.

In another embodiment, the invention is directed to a method comprising: generating in a computer memory a three dimensional digital rendering of a dental restoration; generating in the computer a digital rendering of a blank volume, the blank volume corresponding in dimensions to the usable volume of a blank that is available for milling, and the blank volume having a boundary corresponding to its edges; before the design of a dental restoration is complete, calculating areas of the dental restoration which are beyond the boundary; and providing the calculated areas to a calling function, user, or module.

The details of one or more embodiments of the invention are set forth in the accompanying drawings and the description below. Features, objects, and advantages of the invention will be apparent from the description and drawings, and from the claims.

BRIEF DESCRIPTION OF DRAWINGS

FIG. 5A through FIG. 7 are screenshots of an example implementation of a dental CAD/CAM system including various modules allowing a user to see a blank volume in relation to a dental restoration.

DETAILED DESCRIPTION

Figure 1:
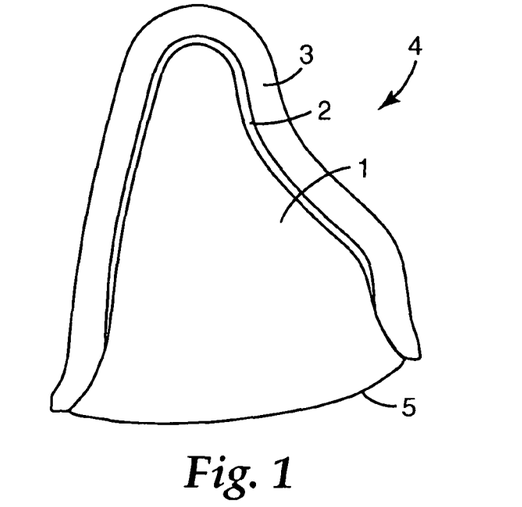
FIG. 1 is a diagram showing an exemplary representation of a dental restoration.

FIG. 1 is a diagram showing an exemplary representation of a dental restoration 4, that includes a coping 3 affixed with an adhesive layer 2 to stump 1. Dental restoration 4 is an artificial tooth, or a partial artificial tooth. Coping 3 refers to the artificial tooth layer. Coping 3 may attach existing dental infrastructure by first grinding down an existing tooth, thus creating stump 1. Coping 3 then fits over and is affixed to stump 1. Dental restoration 4 may form a partial tooth, a full tooth, or multiple teeth. If dental restoration 4 spans an area where a tooth is missing, the restoration of the tooth is termed a pontic, and is part of a larger dental restoration system (termed a bridge) that spans from a stump, includes a pontic, and attaches in most cases to another stump. A pontic restoration includes at least one restoration for which there is no corresponding stump 1. A pontic restoration, then, is attached to adjacent stumps, usually with a dental restoration that is attached to a first stump, spans the area wherein there previously was a tooth, then is again affixed to a second, adjacent stump. As the term is used herein, "stump" refers to one tooth, or multiple teeth, to which a dental restoration may be attached, as the case may be. A "stump landscape" refers to a stump, a partial stump, and adjacent space having no stump, or some combination of stumps and/or partial stumps and/or blank space or teeth defining an area for an eventual restoration. A stump landscape may, as the case may be, additionally refer to associated coping layers and pontics, depending wherein the design process a user is. A stump may also be referred to as a preparation. Stump 1 is shown with preparation line 5. Preparation line 5 is a point beneath which dental restoration 4 does not usually extend. In practice, a porcelain veneer is manually applied to the finished dental restoration, which adds another layer to the coping layer. Since this is not usually done in the CAD/CAM software, and is rather done manually, the porcelain veneer layer is not shown in FIG. 1.

Figure 2:
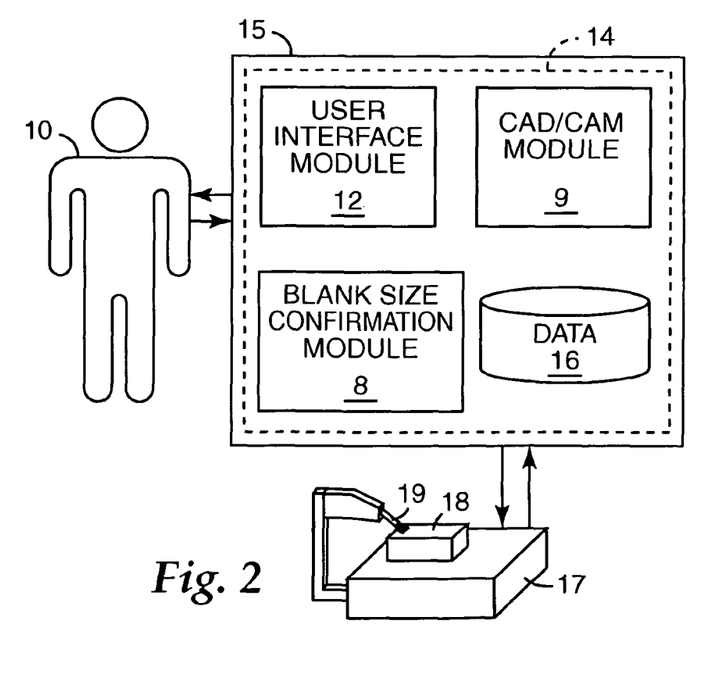
FIG. 2 is a block diagram showing an exemplary implementation of one embodiment of the invention.

FIG. 2 is a diagram showing an exemplary implementation of one embodiment of the invention. User 10 interacts with computing device 15 to use dental CAD/CAM system 14 to design dental restorations. CAD stands for Computer Aided Design, and CAM stands for Computer Aided Manufacturing, or Milling. Computing device 15 interacts with milling machine 17, which mills a model of a dental restoration from blank 18 using cutting device 19. Dental CAD/CAM system 14, in this exemplary embodiment, includes user interface module 12, which presents information to, and receives information from, user 10. CAD/CAM module 9 includes traditional functionality of dental CAD/CAM systems, such as the ability to digitally render a tooth stump, then to design a dental restoration. An exemplary CAD/CAM module 9 is that which is marketed by 3M, of St. Paul, Minn., under the trade designation "LAVA". CAD/CAM module 9 may not be a classic CAD/CAM module, and in certain embodiments is simply not necessary. For example, in one embodiment a user creates a model of a dental restoration out of wax, and then scans it into computer memory. In either of these examples, the CAD/CAM module doesn't exist in a traditional form. In such examples and others, the invention may still be used after the point in which the modeled restoration is digitized and imported into a computer system in anticipation of milling. CAD/CAM module 9 may include three dimensional rendering capabilities such as that provided by OpenGL. OpenGL is a library built into most operating systems. Many video hardware boards provide acceleration for it. Information on OpenGL can be found on www.opengl.org, and information about three dimensional rendering and manipulation may be found at http://www.opengl.org/documentation/red_book/. This link includes the full text of the book "OpenGL Programming Guide: The Official Guide to Learning OpenGL, Version 2 (5th Edition)," by Dave Shreiner, et. al. Further information about rendering images may be found in the following texts: Rost, Randi J. OpenGL(R) Shading Language. 2nd Edition. Boston: Addison-Wesley Professional, 2006; Shreiner, Dave et al. OpenGL(R) Reference Manual: The Official Reference Document to OpenGL, Version 1.4. 4th Edition. Boston: Addison-Wesley Professional, 2004. A commercial library built on OpenGL is OpenInventor by Mercury Computer Systems Inc., Chelmsford, Mass., a manual for which is available at http://www.tgs.com/support/oiv_doc/UsersGuide/UsersGuide.pdf. Other programs available on the Internet teach known three dimensional scanning and rendering techniques. One such program is MeshLab, which is "an open source portable and extendible system for the processing of unstructured 3D triangular meshes. MeshLab is aimed to help the processing of the typical not-so-small unstructured models arising in 3D scanning, providing a set of tools for cleaning, healing, inspecting, rendering and converting this kind of meshes." (Text quoted from MeshLab website). The code for MeshLab, as well as the MeshLab program itself, is available on the Internet as of May 31, 2006, at http://meshlab.sourceforge.net.

Data 16 is a database containing information to be accessed from the various other modules contained in dental CAD/CAM system 14. In one embodiment, data 16 contains information defining a tooth stump and information defining a blank. In one embodiment, data 16 contains information defining many blanks of differing sizes and dimensions. Data 16 may also hold information defining other structures useful in designing a dental restoration, such as various pontics. Blank size confirmation module 8 interacts with data 16 and user interface module 12 to, in one embodiment, graphically render an expected dental restoration, and graphically render the blank, then overlay the blank on top of the expected dental restoration, and thus present areas of the expected dental restoration that exceed the boundary of the blank.

User 10, in one embodiment, is any individual interested in designing, or assisting in designing, a dental restoration. User 10 may be, for example a dental technician, or a dentist.

Milling machine 17 is any machine capable of producing a real model of a dental restoration. Examples include standard milling machines, or those particularly suited for dental milling. One such dental milling machine is that marketed by 3M of St. Paul, Minn., under the trade designation "LAVA FORM." Milling machine 17 includes cutting device 19, which cuts or grinds blank 18 to produce a model of a dental restoration. Milling machine 17, in the exemplary embodiment shown with respect to FIG. 2, is shown holding blank 18. Blank 18 is, for example, any medium into which, or from which, a model of a dental restoration may be created. In one embodiment, blank 18 is a substantially ceramic material. Blank 18 has dimensions, or boundaries, defined by its size, or defined by the maximum working size of milling machine 17. For example, milling machine 17 may, in one embodiment, accept a blank that is larger than it can process. In such a scenario, the blank dimensions are said to be the dimensions as defined by the milling machine's limits. The useable area for a blank is termed the "blank volume". Blank volume may be less than the size of the blank if, for example, particulars of the milling machine or process places limitations on the area that may be milled, or due to other limits set by user 10 or a $3^{rd}$ party (for example, the manufacturer of a blank may not recommend milling within a certain distance of an edge). The blank volume may be substantially round, cylindrical, cubical, or of any shape and dimension. In another embodiment, blank 18 is a medium wherein a model of a dental restoration is created by, for example, traditional milling, thermal cure techniques, stereo lithography, three dimensional printing, or by removing material with lasers.

Computing device 15 typically includes hardware (not shown in FIG. 2) that may include one or more processors, volatile memory (RAM), a device for reading computer-readable media, and input/output devices, such as a display, a keyboard, and a pointing device. Computing device 15 may be, for example, a workstation, a laptop, a personal digital assistant (PDA), a server, a mainframe or any other general-purpose or application-specific computing device. Although not shown, computing device 15 may also include other software, firmware, or combinations thereof, such as an operating system and other application software. Computing device 15 may read executable software instructions from a computer-readable medium (such as a hard drive, a CD-ROM, or a computer memory), or may receive instructions from another source logically connected to computer, such as another networked computer.

Dental CAD/CAM system 14 may be distributed to execute on multiple computers, and may be located remote to user 10 and accessible via a web browser or other distributed interface system.

Data 16, in one embodiment, represents one or more data stores. Data 16 in one embodiment is comprised of databases, may be implemented in a variety of forms including data storage files, computer memory, or one or more database management systems (DBMS) executing on one or more database servers. The database management system may be a relational (RDBMS), hierarchical (HDBMS), multidimensional (MDBMS), object oriented (ODBMS or OODBMS) or object relational (ORDBMS) database management system. Data 16 could, for example, be stored within a single relational database such as SQL Server from Microsoft corporation. In one embodiment, data 16 is a flat file loaded into memory of computing device 15.

User interface module 12 may be any user interface and in one embodiment is a graphical user interface. A graphical user interface is computer program or a module of a computer program designed to allow a user to interact easily with the computer. A graphical user interface typically receives input from a mouse or other pointing device, to make choices from menus or groups of icons. In dental CAD/CAM applications, a graphical user facilitates the presentation of a graphical rendering of a tooth stump, and allows user 10 to manipulate the tooth stump and design a dental restoration.

Figure 3:
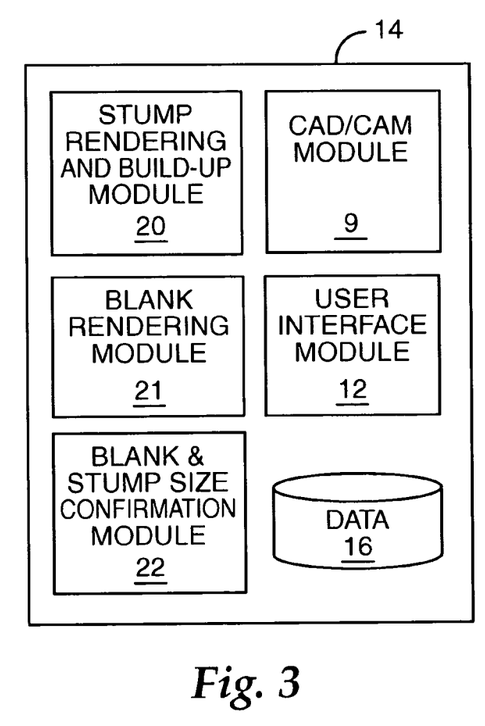
FIG. 3 is a block diagram showing software and database modules that, in one embodiment, comprise a dental CAD/CAM system.

FIG. 3 is a diagram showing an exemplary embodiment of various software modules that may comprise dental CAD/CAM system 14. Included is data 16, user interface module 12, and CAD/CAM module 9, all of which were discussed earlier. In FIG. 3, blank size confirmation module 8 is shown with exemplary constituent modules. Blank size confirmation module 8, depending on particulars of the implementation, may communicate and interact directly with user interface module 12 and data 16, or may communicate and interact with either or both via CAD/CAM module 9. In one embodiment, blank size confirmation module 8 makes function calls to functionality in CAD/CAM module 9.

In the exemplary embodiment shown in FIG. 3, blank size confirmation module 8 is shown with three sub-modules. Stump rendering and build-up module 20 renders a graphical model, or rendering, of a tooth stump, from information housed in data 16 that describes the tooth stump. Information housed in data 16 that describes the tooth stump is typically generated from scanning device, which scans a model of a tooth stump in three dimensions. The scanning device may be any device that can digitally render an object. Such scanning devices may be optical, mechanical, X-ray, or so forth. The scanning device produces digital information that defines the tooth stump. In one embodiment, the graphical rendering is three dimensional. Stump rendering and build up module 20 may, in one example embodiment, cause user interface module 12 to display the graphical rendering directly, or it may provide information describing the graphical rendering to CAD/CAM module 9, which in turn provides the information to user interface module 12.

Blank rendering module 21 renders a graphical model, or rendering, of blank 18 or the blank volume of blank 18. In one embodiment the graphical rendering is three dimensional. When the blank is of uncomplicated dimensions, its three dimensional digital rendering is a straightforward and accommodated by basic CAD/CAM functionality such as that available in CAD/CAM module 9.

Blank and stump size confirmation module 22 receives data defining a graphical rendering of a stump, as in one embodiment is provided by stump rendering and build-up module 20. Blank and stump size confirmation module 22 also, in one embodiment, receives data defining a graphical rendering of a blank, as in one embodiment is provided by blank rendering module 21. Blank and stump size confirmation module 22 analyzes these two sets of information and attempts to fit the graphical rendering of the stump within the graphical rendering of the blank. Blank and stump size confirmation module 22 may request stump rendering and build-up module 20 to apply a coping comprised of one or more layers to various areas of the graphical rendering of the stump, so as to account for the dimensional thickness of the eventual designs of the dental restoration.

Blank and stump size confirmation module 22 may determine areas of the graphical rendering of the stump that extend beyond the dimensions of the graphical rendering of the blank. The fact that areas of the graphical rendering of the stump extend beyond the dimensions of the graphical rendering of the blank are, in one embodiment, communicated to the user. In another embodiment, information defining both the graphical representation of the stump and a graphical representation of the blank are presented to user 10 via user interface module 12. Areas of the graphical representation of the stump that extend beyond the dimensions of graphical rendering of the blank in one embodiment are assigned a visual indicia, such as a color or shading, that is relatively distinct from the graphical rendering of the stump or the blank, such that the area extending beyond the dimensions of the blank are identifiable by user 10 by interacting with user interface module 12.

Figure 4:
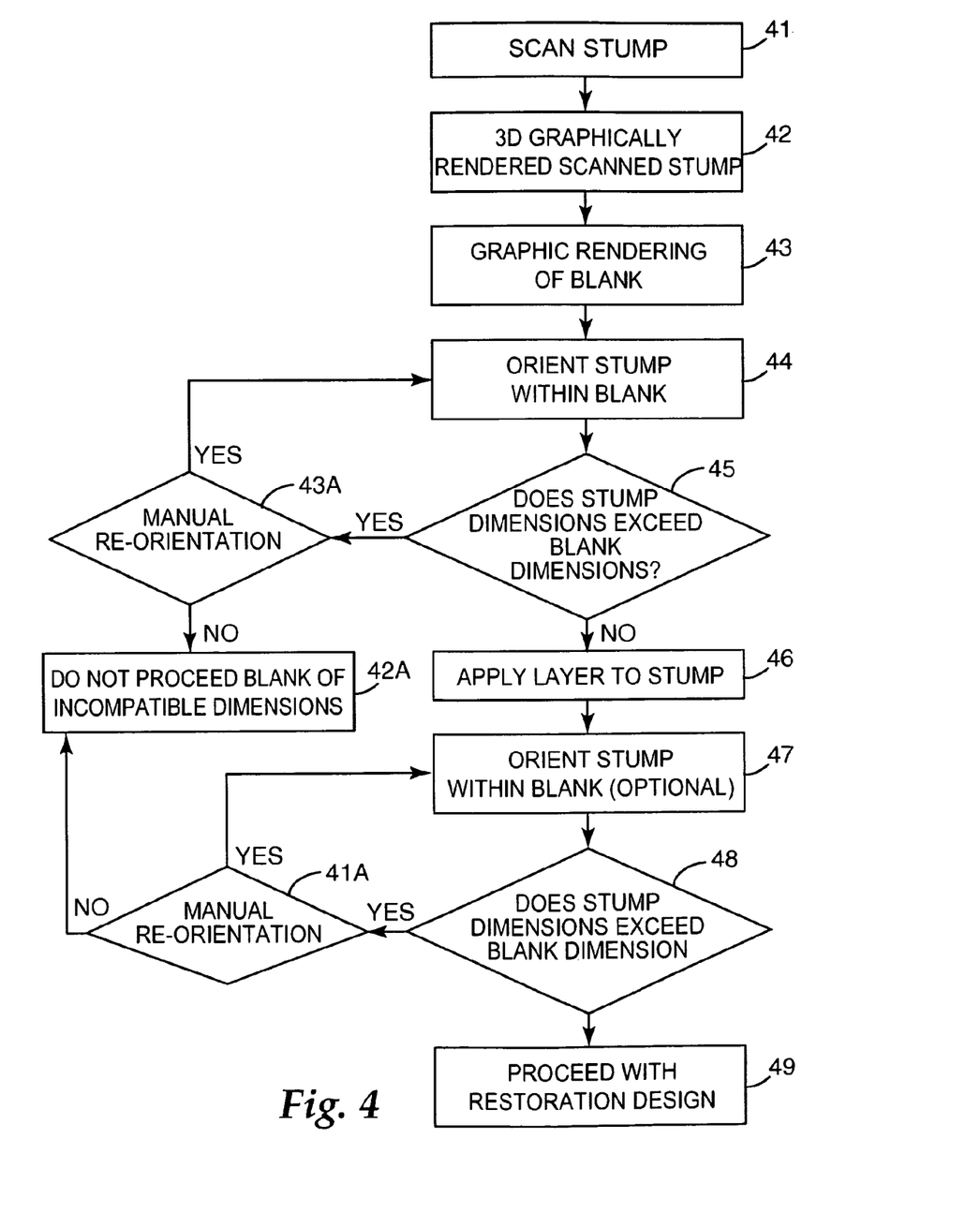
FIG. 4 is a flowchart showing an exemplary manner in which a dental CAD/CAM system may check for areas of a dental restoration that extend beyond the dimensions of a blank's usable volume.

FIG. 4 is a flowchart showing an exemplary manner in which dental CAD/CAM system 14 may check for areas of the dental restoration that extend beyond the dimensions of the blank volume. First, the stump is scanned (41). Stump scanning may be accomplished by myriad tooth scanners available on the market, such as that marked by 3M of St. Paul, Minn., under the trade designation "LAVA SCAN", or a general purpose scanner such as that marketed by "GOM—Gesellschaft für Optische Messtechnik mbH", of Braunschweig, Germany, under the trade designation "ATOS SO." The stump scanning device outputs, for example, a digital description of the stump landscape, which is then graphically rendered in three dimensions to produce a graphic of the stump landscape (42). After the stump is scanned, dental CAD/CAM system 14, and particularly blank size confirmation module 8 and its associated sub-modules, carry out the bulk of the remaining processes diagrammatically shown with respect to FIG. 4. Stump scanning (41) and graphical rendering (42) need not be done at the same time, or at the same location. In order to graphically render the stump, in one embodiment the minimum that is necessary is a digital description of the stump landscape, as could be provided, for example, in a computer-readable file, such as that that might be produced by scan stump (41), particularly if the scanning device was not in direct communication with computing device 15. The graphical rendering of the stump landscape is facilitated by stump rendering and build-up module 20, which is shown with respect to FIG. 3. Stump rendering and build-up module 20 accesses, in one embodiment, functionality contained within most CAD/CAM modules to do the actual graphical rendering and subsequent manipulation. In such an embodiment, stump rendering and build-up module 20 facilitates initial rendering, and subsequently receives input, as from a user, and where necessary interacts with CAD/CAM module 9 to modify or update the graphical rendering. Typically, commercially available CAD/CAM modules, such as those mentioned earlier, may receive a digital description of a two or three dimensional figure and render it into a graphic representation, which may then be displayed via a user interface, such as that contained in user interface module 12. The ability to receive a file conforming to a digital description standard, and then rendering that digital description into a graphic is functionality contained in exemplary CAD/CAM module 9 shown with respect to FIG. 3. An alternative implementation might include a custom module for receiving and graphically rendering a stump landscape, and thus not take advantage of the native functionality of CAD/CAM module 9 or similar CAD/CAM modules.

Next, blank size confirmation module 8 invokes blank rendering module 21 to render a three dimensional graphical rendering of the blank volume (43). This graphical rendering is overlaid upon the graphical rendering of the scanned stump landscape, described above. Available blanks, with their associated blank volumes, in one embodiment, are stored in data 16. If there are multiple blanks, with differing blank volumes, available, user 10 may be prompted to select a blank among those available. Alternatively, the blank may be automatically selected by dental CAD/CAM system 14 or blank size confirmation module 8 based on dimensions used by stump rendering and build-up module 20 in graphically rendering the stump landscape. In one embodiment the automatic selection of a blank is done by blank size confirmation module 8, by measuring the widest dimensions of the stump or stumps the restoration will encompass, then adding a value representative of a traditional build-up. In one embodiment this is ½ of a millimeter. Blank size confirmation module 8 then iterates through data describing available blanks, checking whether the dimensions of the expected restoration will fit within the blank. The smallest blank that the dental restoration will presumptively fit within is automatically chosen. User 10 may override this automatic choice, or may, in one embodiment, alter the build-up value and then instruct blank size confirmation module 8 to automatically select another blank.

Figure 6:
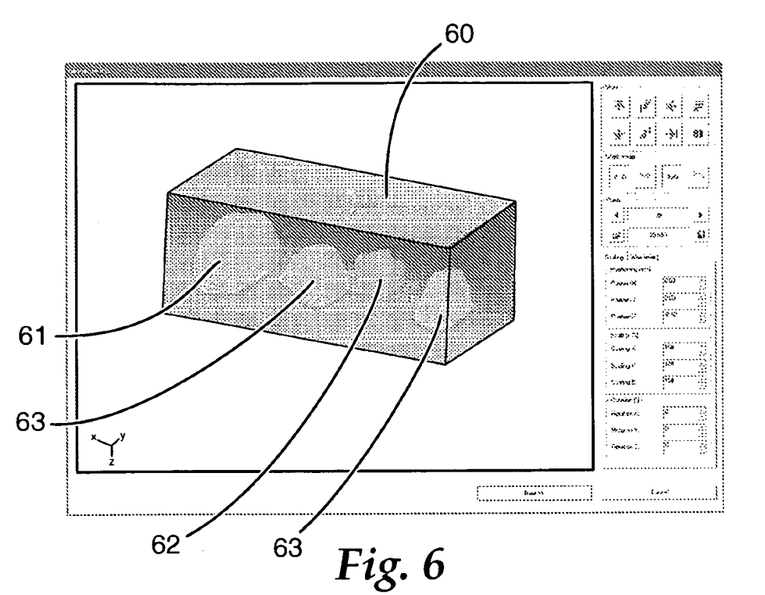

As mentioned above, the graphical rendering of the blank volume is overlaid upon the graphical rendering of the stump landscape. FIG. 6 is a screenshot of such an overlay. Stumps 61 and 63, as well as pontic 62, comprise the stump landscape. Pontic 62 is typically held within, and selected from, a library of pontics in data 16. It may, however, be scanned in, in one embodiment. Three dimensional graphical rendering 60 shows the blank volume. To user 10, the stump landscape appears to be substantially within the blank volume. The combination of these two three dimensional forms (the stump landscape and the blank volume) is done by setting the graphical rendering of the blank volume properties to transparent, then orienting the stump landscape within the blank volume.

Next, the stump landscape is oriented within the blank volume (44). In one embodiment blank size confirmation module 8 facilitates this orientation by soliciting input from user 10 as to movements of the stump landscape along the X, Y, or Z axis defined by the graphical rendering of the blank volume. In one embodiment, a cursor in communication with a pointing device, such as a mouse, seemingly attaches to a point on the stump landscape, and may be rotated by moving the pointing device. User 10 may exercise various control buttons and settings as shown on the right side of FIG. 6 to alter the perspective shown in the graphical user interface. For example, user 10 may instruct blank size confirmation module 8 to show the graphical rendering of the stump landscape and blank volume from the top, bottom, or another side. Changes in the perspective, as well as changes in the orientation of the stump landscape within the blank volume, are facilitated by blank size confirmation module 8 via API and function calls to native 3D rendering and manipulation functionality as contained within CAD/CAM module 1.

The stump landscape orientation within the blank volume may also be accomplished automatically by blank size confirmation module 8. One exemplary manner of automatically orienting the stump landscape is as follows. A bounding box, which just encompasses the stump landscape, is computed by blank size confirmation module 8. The bounding box, and thus the stump landscape, are then oriented within the blank volume by applying approximately uniform dimensions to distances from the bounding box to the boundary of the blank volume. Another approach is to calculate the centroid of the blank volume and the stump landscape objects, then align these centroids in three dimensions. Alternatively, one can calculate the center of both the blank volume and the bounding box in the X, Y, and Z dimension, and center the stump landscape within the blank volume in each dimension.

If areas of the stump landscape exceed the dimensions of the blank volume, the area outside of the blank volume is in one embodiment assigned a visual indicia distinct in appearance from the graphical representation of the stump landscape and the blank volume. In one embodiment, the visual indicia is a color. In another embodiment, the protruding area is not explicitly assigned a different color by blank size confirmation module 8 via blank & stump size confirmation module 22, but is instead native functionality of the blank volume as provided by CAD/CAM module 1. For example, in one embodiment, the nature of the blank volume rendering is such that it appears partially transparent, with a visual appearance that allows objects oriented within the blank volume to be seen as opaque. The nature of the blank volume's transparency, and particularly the opaqueness, does not apply to areas that extend beyond the blank volume. In this way, blank size confirmation module 8 may not explicitly request CAD/CAM module 9 to color areas extending beyond the dimensions of blank volume differently—rather, blank size confirmation module 8, in one embodiment, need only to specify the nature of the semi-transparent graphical rendering of the blank volume, and the opaque filter. Then, areas protruding from the blank volume are simply not opaque; they are instead the defined color of the stump landscape. This approach may avoid complex calculations, and may allow fast operation of dental CAD/CAM system 14 generally, and blank size confirmation module 8 specifically.

Further embodiments do not require any graphical rendering displayed to a user, and instead may result in a returned function call telling whether, and the extent to which, a stump landscape extends beyond a blank volume. In such an embodiment, the supporting calculations are the same, absent those supporting display to a user via a user interface.

Figure 7:
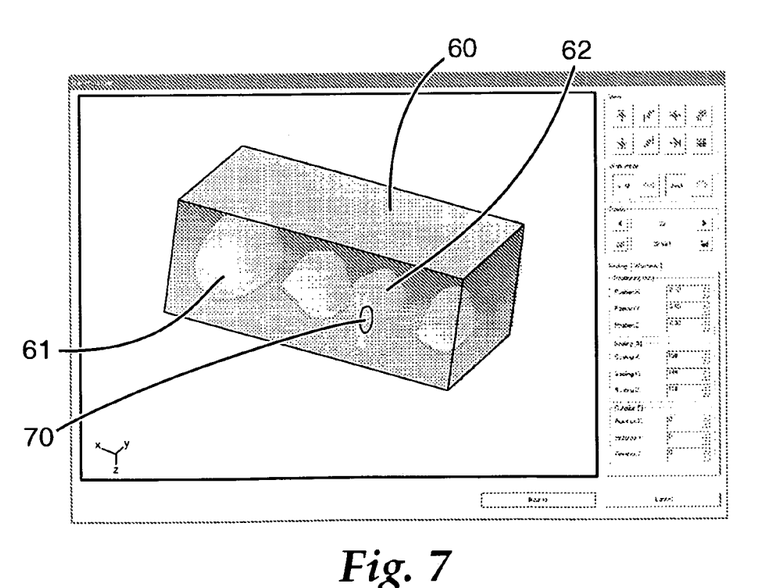

User 10 then, in one embodiment, determines whether any areas of the stump landscape extend beyond the dimensions of the blank volume. FIG. 6 shows a screenshot wherein the stump landscape is all inside of the blank volume. FIG. 7 shows a screenshot from dental CAD/CAM system 14 wherein extended area 70 of pontic 62 extends beyond the front face of blank volume 60. With no opaque filter applied to extended area 70, extended area 70 appears distinct from other areas of stump landscape that are within the dimensions of blank volume. By looking for areas of the graphical rendering of the stump landscape that appear in color or other visual indicia distinct from other areas of the stump landscape, user 10 may determine whether the stump landscape exceeds the blank volume dimensions (45). Alternatively, this determination may be done automatically by via a function call to the blank rendering module 20 asking whether, and the location of, areas protrude from the graphical rendering of blank volume. This function call is done, in one embodiment, from blank & stump size confirmation module 22. If areas of stump landscape are found to protrude from blank volume, user 10 may decide to manually re-orient the stump landscape in relation to the blank volume (43A), in which case user 10 again orients the stump landscape within blank volume (44). Though not represented with respect to FIG. 4, user 10 may proceed with subsequent analysis and design activities even if an area of the stump landscape extends beyond the blank volume. User 10 may do this, for example, if user 10 is confident that the protruding area is not critical, or represents an error that can be manually addressed in the design process. In the example represented by FIG. 4, however, user 10 seeks a stump landscape that does not protrude from the blank volume. If user 10 cannot achieve this, either manually or automatically, the blank may be determined by user 10 to be of an incompatible size and opt not to proceed, or start over with a different approach altogether (42A) (no at manual re-orientation (43A)).

Assuming user 10 is able to achieve an orientation of stump landscape within the boundaries of blank volume, user 10 may indicate such via user interface module 12, and then a layer is applied to the stumps in the stump landscape (46). The layer's thickness may be specified by user 10, and in one embodiment must be at least 0.5 millimeters, which is the minimum depth of coping 3, usually specified by the manufacturer of the coping. The application of the layer is facilitated by stump rendering and build-up module 22, via function and/or API calls to native functionality within CAD/CAM module 1. The layer helps approximate the eventual build-up of the stump that will take place in the design process, and thus approximate the eventual size of the dental restoration to be milled from the blank. User 10 often knows, roughly at least, the thickness of various areas of the dental restoration. User 10 may, then, apply additional layers or partial layers to areas of the stump or stumps comprising the stump landscape, to build up whatever thicknesses user 10 deems representative of the eventual dental restoration.

Next, user 10 may, if necessary, again orient the stump within the blank (47). User 10 may, however, determine that additional orientation is not necessary. User 10 then determines whether the stump landscape protrudes from the blank volume (48), in the same manner as described above with respect to the identically entitled control box 45. Like in the previous box, though not shown with respect to FIG. 4, user 10 may decide to proceed with the design of the dental restoration even though an area extends beyond the dimensions of the blank volume. In such a manner, user 10's ability to see the blank volume relative to the stump landscape in and of itself may provide information that is useful.

In this example illustrated by FIG. 4, however, the stump landscape is intended to fit within blank volume. Thus, if areas of stump landscape protrude from blank volume, user 10 is given the opportunity to modify various parameters (41A). Such parameters may include revisiting the thickness of layers applied earlier, the relative position of components of the dental restoration (for example, it is possible to move pontic 63 backwards relative to the orientation of stumps 61 and 63). Additionally, user 10 may specify dental CAD/CAM system 10 to merely eliminate areas protruding from the blank volume.

With various parameters modified, user 10 may again orient the stump within the blank volume (47), and continue to loop in this manner until satisfied. However, if user 10 determines it is no longer helpful to modify parameters (41A), user 10 may determine the blank volume is simply of dimensions incompatible with the expected dimensions of the dental restoration (42A).

If user 10 is, however, able to successfully orient stump landscape within blank volume, user 10 may proceed with the restoration design (49), thus leaving functionality contained within blank size confirmation module 8.

The process described with respect to FIG. 4 has been described as being invoked before any substantive design of the eventual dental restoration has been completed, but this is for exemplary purposes only. Blank size confirmation module 8 may be similarly invoked at any stage during the design process. If invoked later, substantially the same process as shown in FIG. 4 could be used, but the initial stump landscape would be the current state of the dental restoration rather than the scanned stump or stumps, and all layers applied to the stump (46) would be explicitly defined by user 10 (in the embodiment described with respect to FIG. 4, a layer equal in thickness to the minimum thickness of a coping layer may be automatically applied).

Figure 5A:
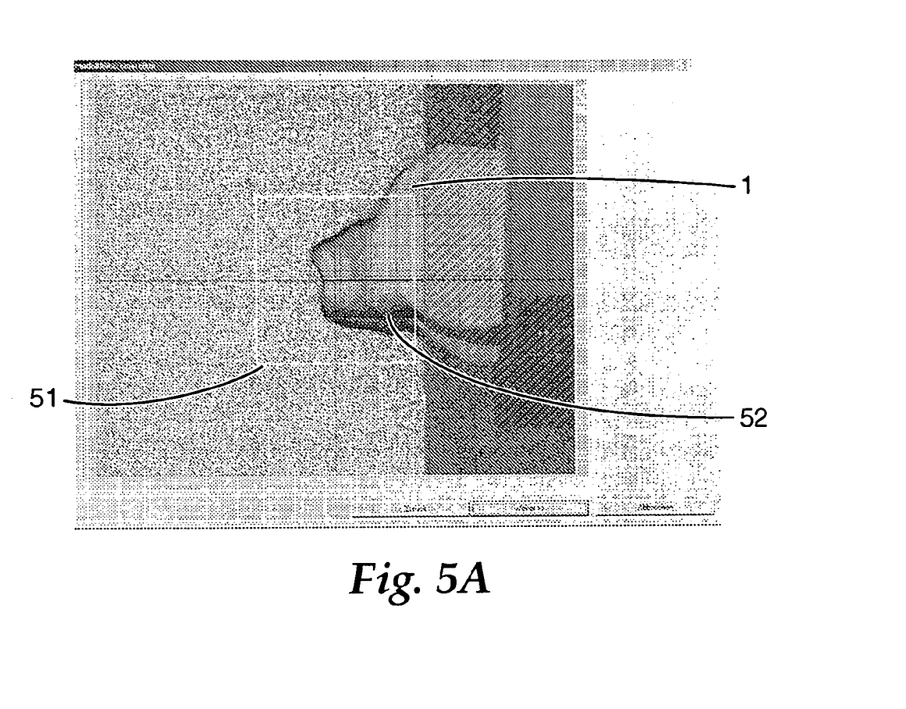

FIG. 5A is an exemplary screen shot showing one embodiment of dental CAD/CAM system 14 wherein stump 1 has been graphically rendered per stump rendering and build-up module 20. Blank rendering module 21, in this exemplary view, has generated a two dimensional graphical representation 51 of blank 8's blank volume, which has been combined and overlaid upon the graphical rendering of stump 1 per blank and stump size confirmation module 22. The graphical interface is presented by user interface module 12. In one embodiment, this check using a two dimensional rendering of blank 8 is a first check made before the application of a coping layer, and is followed by a check using a three dimensional rendering of blank 8. User 10 may, in one embodiment, manipulate the orientation of stump 1 in relation to the two-dimensional graphical rendering of the blank, or may request dental CAD/CAM system 14 to automatically orient stump 1. For reference purposes, preparation line 52 can be viewed on the graphical representation of the tooth stump. Coping layer 1 generally caps stump 1 and terminates at preparation line 52. For this reason, subsequent three dimensional renderings of stump 1 may terminate the tooth at the preparation line.

Figure 5B:
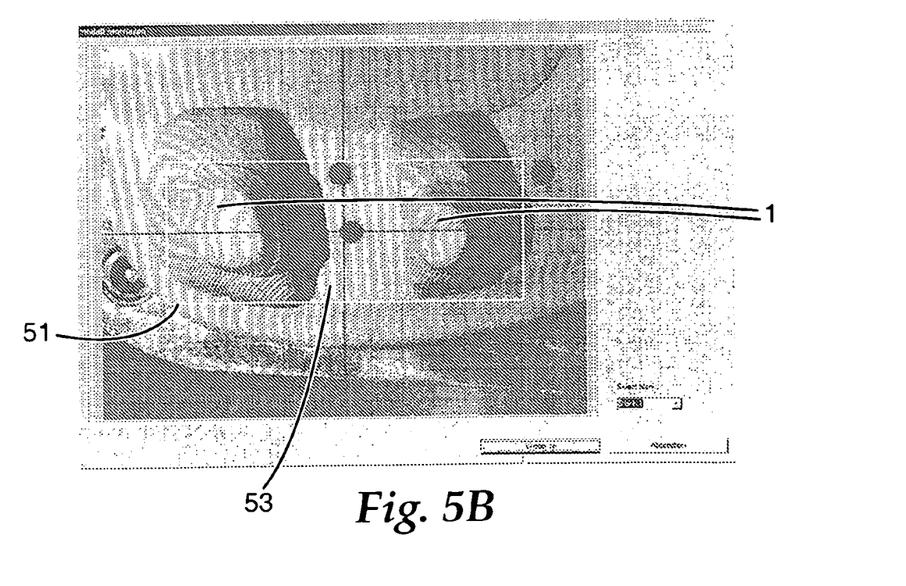

FIG. 5B is an exemplary screen shot showing a different angle of stump 1 as shown with respect to FIG. 5A. The perspective in FIG. 5B is from the top, looking down upon the tooth stumps. The two dimensional graphic representation 51 of blank 8's blank volume is similarly overlaid in this figure. Pontic area 51 shows that there is a gap that must receive a pontic.

FIG. 6 is an exemplary screen shot showing one embodiment of dental CAD/CAM system in designing a pontic. Stumps, in this screen shot, have been overlaid with a coping layer of 0.5 mm and terminated at the preparation line. User 10 may modify the size of the coping layer by interacting with user interface 12. Additionally, particular areas of the stump may be identified where a thicker coping layer is requested. In one embodiment, the coping layer may be specified up to 1 mm. The "built-up" dental restoration is, then, shown with respect to dental restoration 61 and 63. The two dental restorations 63 form a pontic with dental restoration 62. In this exemplary screenshot, the graphical rendering of blank 8 is shown in three dimensional graphical rendering 60. User 10 may orient the dental restoration within three dimensional graphical rendering 60. She may also change the thickness the coping layer, the orientation of the pontic relative to the other tooth stumps.

FIG. 7 is an exemplary screen shot showing one embodiment of dental CAD/CAM system in designing a dental restoration with a pontic. The screen shot is similar to that in FIG. 6, except in this case one area of the dental restoration extends beyond the dimensions of blank 8. The area extending beyond the area of blank 8 is out-of-bounds area 70. The graphical representation of out-of-bounds area 70 is shown assigned a visual indicia of a color or shading distinct from the three dimensional graphical rendering of blank 8 and three dimensional graphical rendering of stump 1 with coping layer 3. User 10 may then see that the two dimensions are incompatible and alter the orientation of parts of the dental restoration, attempt to account for the incompatible dimensions in the subsequent design of the dental restoration.

This and other embodiments are within the scope of the invention, as one skilled in the art will recognize. Particularly, and for example, the same concepts taught herein could be applied to a two dimensional graphical rendering, though the examples specifically described herein regard three dimensional graphical rendering.

The invention claimed is:

1. A non-transitory computer-readable medium having computer-readable instructions which implement the following procedures:
    generating in a user interface a three dimensional graphical rendering of a dental restoration;
    generating in the user interface a three dimensional graphical rendering of a blank volume, the blank volume corresponding in dimensions to a useable portion of a blank that can be used for milling, wherein the graphical rendering of the blank volume is overlaid upon the three dimensional graphical rendering of the dental restoration such that the three dimensional graphical rendering of the dental restoration appears substantially inside of the three dimensional graphical rendering of the blank volume;
    based on the three dimensional graphical rendering of the blank volume overlaid upon the three dimensional graphical rendering of the dental restoration, calculating a portion of the dental restoration extends beyond a boundary of the blank volume; and,
    presenting to a user via the user interface, three dimensional graphical rendering of the blank volume and the three dimensional graphical rendering of the dental restoration to facilitate the user to determine how to proceed with the blank volume, wherein the three dimensional graphical rendering of the portion of the dental restoration that extends beyond the boundary of the blank volume has been assigned a visual indicia, wherein the blank volume has been overlaid upon the three dimensional graphical rendering of the dental restoration, soliciting input from a user defining a design for a dental restoration.

2. The non-transitory computer-readable medium of claim 1, wherein the portion of the three dimensional graphical rendering of the dental restoration that extends beyond the boundary of the three dimensional blank volume is presented in a way such that the user can identify at least one portions of the three dimensional graphical rendering of the dental restoration that extend beyond the boundary of the three dimensional graphical rendering of the blank volume.

3. The non-transitory computer-readable medium of claim 1, wherein the three dimensional graphical rendering of the blank volume allows the three dimensional graphical rendering of the dental restoration to be viewed inside of the blank volume.

4. The non-transitory computer-readable medium of claim 1, wherein assigning visual indicia is done before the dental restoration is designed.

5. The non-transitory computer-readable medium of claim 1, wherein assigning visual indicia is done before the dental restoration is designed.

6. The non-transitory computer-readable medium of claim 1, wherein the dental restoration is a tooth stump or stump landscape.

7. The non-transitory computer-readable medium of claim 1, wherein the dental restoration is comprised of one or more layers.

8. The non-transitory computer-readable medium of claim 7, wherein at least one of the layers is greater than 0.2 millimeters.

9. The non-transitory computer-readable medium of claim 1, wherein the blank volume is a prismatic or cylindrical shape.

10. A method comprising: a processor couple to a memory;
    generating in a user interface a three dimensional graphical rendering of a dental restoration;
    generating in the user interface a three dimensional graphical rendering of a blank volume, the blank volume corresponding in dimensions to a useable portion of a blank that can be used for milling, wherein the three dimensional graphical rendering of the blank volume is overlaid upon the three dimensional graphical rendering of the dental restoration such that the three dimensional graphical rendering of the dental restoration appears substantially inside of the three dimensional graphical rendering of the blank volume;
    based on blank volume overlaid upon the three dimensional graphical rendering of the dental restoration, calculating a portion of the dental restoration extends beyond a boundary of the blank volume; and,
    presenting to a user via the user interface, three dimensional graphical rendering of the blank volume and the three dimensional graphical rendering of the dental restoration to facilitate the user to determine how to proceed with the blank volume, wherein the three dimensional graphical rendering of the portion of the dental restoration that extends beyond the boundary of the blank volume has been assigned a visual indicia, wherein the blank volume has been overlaid upon the three dimensional graphical rendering of the dental restoration, soliciting input from a user defining a design for a dental restoration.

11. The method of claim 10, further comprising:
presenting to a user via the user interface the three dimensional graphical rendering of the blank volume and the three dimensional graphical rendering of the dental restoration, wherein the portion of the three dimensional graphical rendering of the dental restoration that extends beyond the boundary of the blank volume is presented in a way such that the user can identify portions of the three dimensional graphical rendering of the dental restoration that extend beyond the dimensions of the three dimensional graphical rendering of the blank volume.

12. The method of claim 10, wherein the three dimensional graphical rendering of the blank volume allows the three dimensional graphical rendering of the dental restoration to be viewed inside of the blank volume.

13. The method of claim 10, wherein automatically assigning visual indicia is done before the dental restoration is designed.

14. The method of claim 10, wherein the visual indicia is a color or texture.

15. The method of claim 10, wherein the dental restoration is a tooth stump or stump landscape.

16. The method of claim 10, wherein the dental restoration is comprised of one or more layers.

17. The method of claim 16, wherein at least one of the layers is greater than 0.2 millimeters.

18. The method of claim 10, wherein the blank volume is a prismatic or cylindrical shape.

* * * * *

UNITED STATES PATENT AND TRADEMARK OFFICE
CERTIFICATE OF CORRECTION

Page 1 of 1

PATENT NO. : 9,026,238 B2
APPLICATION NO. : 12/373206
DATED : May 5, 2015
INVENTOR(S) : Kraemer et al.

It is certified that error appears in the above-identified patent and that said Letters Patent is hereby corrected as shown below:

In the Claims

Col. 12, line 11, in Claim 2, delete "portions" and insert --portion--.

Signed and Sealed this
Twenty-second Day of December, 2015

Michelle K. Lee
*Director of the United States Patent and Trademark Office*